United States Patent
Obias

(10) Patent No.: US 10,905,639 B2
(45) Date of Patent: Feb. 2, 2021

(54) TOOTH WHITENING COMPOSITION

(71) Applicant: Chattem Inc., Chattanooga, TN (US)

(72) Inventor: Honorio Velasco Obias, Chattanooga, TN (US)

(73) Assignee: CHATTEM, INC., Chattanooga, TN (US)

( * ) Notice: Subject to any disclaimer, the term of this patent is extended or adjusted under 35 U.S.C. 154(b) by 0 days.

(21) Appl. No.: 16/724,318

(22) Filed: Dec. 22, 2019

(65) Prior Publication Data

US 2020/0214949 A1    Jul. 9, 2020

Related U.S. Application Data

(60) Provisional application No. 62/788,454, filed on Jan. 4, 2019.

(51) Int. Cl.
| | | |
|---|---|---|
| *A61K 8/22* | (2006.01) | |
| *A61K 8/368* | (2006.01) | |
| *A61K 8/34* | (2006.01) | |
| *A61Q 11/00* | (2006.01) | |
| *A61K 8/60* | (2006.01) | |
| *A61K 8/55* | (2006.01) | |
| *A61K 8/21* | (2006.01) | |

(52) U.S. Cl.
CPC .................. *A61K 8/22* (2013.01); *A61K 8/21* (2013.01); *A61K 8/34* (2013.01); *A61K 8/345* (2013.01); *A61K 8/368* (2013.01); *A61K 8/55* (2013.01); *A61K 8/60* (2013.01); *A61Q 11/00* (2013.01)

(58) Field of Classification Search
CPC ... A61K 8/34; A61K 8/27; A61K 8/19; A23C 9/1307
USPC ........................................ 424/49, 57; 514/31
See application file for complete search history.

(56) References Cited

U.S. PATENT DOCUMENTS

| | | | |
|---|---|---|---|
| 5,084,268 A * | 1/1992 | Thaler | A61K 8/22 424/53 |
| 9,060,943 B2 * | 6/2015 | Vielhaber | A61P 17/00 |
| 2010/0190735 A1 * | 7/2010 | Bhasin | A61Q 11/00 514/31 |
| 2016/0324741 A1 * | 11/2016 | Baig | A61K 8/27 |

* cited by examiner

*Primary Examiner* — Walter E Webb
(74) *Attorney, Agent, or Firm* — Hylton-Rodic Law PLLC

(57) ABSTRACT

Disclosed are oral care compositions which provide faster and enhanced whitening efficacy. The present compositions comprise a unique combination of whitening agent, gum soother and sodium benzoate.

17 Claims, No Drawings

TOOTH WHITENING COMPOSITION

TECHNICAL FIELD

The present invention is related to a tooth whitening composition comprising a unique combination of whitening agent, gum soother and sodium benzoate.

BACKGROUND OF THE INVENTION

There are a variety of compositions described in the art for preventing or treating the discoloration of teeth. For example, there are whitening products available for dental office applications, for use at home under dentist supervision, and over-the-counter whiteners. Some users of these products develop gum irritation, especially if whitening strips or other whitening products are in contact with the user's gums for an extended period of time. Also, many users experience a little tooth sensitivity from these whitening products.

A cost effective and convenient way to whiten teeth is to use a whitening mouthwash at home. This kind of mouthwash typically contains a bleaching agent, commonly known as hydrogen peroxide. For sensitive users, even a 2.5% hydrogen peroxide solution used in typical whitening mouthwashes can be caustic and irritating. The longer the hydrogen peroxide stays on the teeth, the more whitening efficacy is achieved but the more uncomfortable the experience will be for the user due to the caustic and irritating properties of hydrogen peroxide on nearby oral and gum tissues. A variety of commercial mouthwash are available including CREST®-brand mouthwashes (Procter & Gamble; Cincinnati, Ohio), COLGATE®-brand mouthwashes (Colgate; New York, N.Y.) and LISTERINE®-brand mouthwash (Warner-Lambert Co.; Morris Plains, N.J.). The effectiveness and comfortableness of using currently available products on a daily basis depends on the type and intensity of the stain, the type of bleaching agent, contact time and contact concentration of the bleaching agent on the teeth, and overall user experience.

Accordingly, daily tooth whitening can be an uncomfortable or painful daily experience. Therefore, it would be highly desirable to provide a tooth whitening composition (such as a mouthwash formulation) which provides a fast and efficient whitening experience with less and pain and which can promote gingival health.

SUMMARY OF THE INVENTION

It has been discovered that a tooth whitening composition comprising a combination of sodium benzoate, 4-tert-butylcyclohexanol and hydrogen peroxide provides faster and efficient whitening. One advantage of the invention is the whitening composition can stay in contact with the teeth and oral/gum tissues for a longer time and be used in higher concentrations than comparable commercially available whitening agents.

In an embodiment provided herein, there is a tooth whitening composition comprising:
  a) from about 1.0% to about 5.0% by weight of hydrogen peroxide;
  b) from about 0.1% to about 1.0% by weight of sodium benzoate;
  c) from about 0.01% to about 0.5% by weight of 4-tert-butylcyclohexanol; and
  an orally acceptable formulation component.

In another embodiment provided herein, the tooth whitening composition comprises:
  a) from about 1.0% to about 5.0% by weight of hydrogen peroxide;
  b) from about 0.1% to about 1.0% by weight of sodium benzoate;
  c) from about 0.01% to about 0.5% by weight of 4-tert-butylcyclohexanol; wherein the composition optionally comprises sodium fluoride and has a buffered pH of about 5.5 to about 8, or of about 6 to about 7, or about 6.

In another embodiment provided herein, the tooth whitening composition comprises:
  a) about 5.0% by weight of hydrogen peroxide;
  b) about 0.5% by weight of sodium benzoate;
  c) from about 0.01% to about 0.5% by weight of 4-tert-butylcyclohexanol;
  wherein the composition optionally comprises 0.02% sodium fluoride and has a buffered pH of about 5.5 to about 8, or of about 6 to about 7, or about 6. The trans-4-tert-butylcyclohexanol may be solubilized in pentylene glycole (e.g., SymSitive® by Symrise AG).

In another embodiment provided herein, the tooth whitening composition comprises:
  a) about 2.5% by weight of hydrogen peroxide;
  b) about 0.5% by weight of sodium benzoate;
  c) from about 0.06% by weight of 4-tert-butylcyclohexanol;
  wherein the composition optionally comprises 0.02% sodium fluoride and has a buffered pH of about 5.5 to about 8, or of about 6 to about 7, or about 6. The trans-4-tert-butylcyclohexanol may be solubilized in pentylene glycole (e.g., SymSitive® by Symrise AG).

In another embodiment provided herein, there is a tooth whitening composition comprising:
  a) from about 1.0% to about 5.0% by weight of hydrogen peroxide;
  b) from about 0.1% to about 1.0% by weight of sodium benzoate;
  c) from about 0.01% to about 0.5% by weight of 4-tert-butylcyclohexanol; and
  d) from about 0.01% to about 0.05% by weight of sodium fluoride.

In another embodiment provided herein, there is a tooth whitening composition comprising:
  a) from about 1.0% to about 5.0% by weight of hydrogen peroxide;
  b) from about 0.1% to about 1.0% by weight of sodium benzoate;
  c) from about 0.01% to about 0.5% by weight of 4-tert-butylcyclohexanol;
  d) from about 0.01% to about 0.05% by weight of sodium fluoride;
  e) from about 5.0 to about 15.0% by weight of glycerin;
  f) from about 1.0 to about 5.0% by weight of xylitol;
  g) from about 1.0 to about 3.0% by weight of propylene glycol; and
  h) from about 1.0 to about 3.0% by weight of poloxamer 407.

In another embodiment provided herein, there is a tooth whitening composition comprising:
  a) from about 1.0% to about 5.0% by weight of hydrogen peroxide;
  b) from about 0.1% to about 1.0% by weight of sodium benzoate;
  c) from about 0.01% to about 0.5% by weight of 4-tert-butylcyclohexanol;

d) from about 0.01% to about 0.05% by weight of sodium fluoride;
e) from about 5.0 to about 15.0% by weight of glycerin;
f) from about 1.0 to about 5.0% by weight of xylitol;
g) from about 1.0 to about 3.0% by weight of propylene glycol;
h) from about 1.0 to about 3.0% by weight of poloxamer 407;
i) from about 0.01 to about 0.3% by weight of monosodium phosphate; and
j) from about 0.005 to about 0.2% by weight of disodium phosphate.

In another embodiment provided herein, there is a tooth whitening composition comprising:
a) from about 1.0% to about 5.0% by weight of hydrogen peroxide;
b) from about 0.1% to about 1.0% by weight of sodium benzoate;
c) from about 0.01% to about 0.5% by weight of 4-tert-butylcyclohexanol;
d) from about 0.01% to about 0.05% by weight of sodium fluoride;
e) from about 5.0 to about 15.0% by weight of glycerin;
f) from about 1.0 to about 5.0% by weight of xylitol;
g) from about 1.0 to about 3.0% by weight of propylene glycol;
h) from about 1.0 to about 3.0% by weight of poloxamer 407;
i) from about 0.01 to about 0.3% by weight of monosodium phosphate;
j) from about 0.005 to about 0.1% by weight of menthol;
k) from about 0.005 to about 0.2% by weight of disodium phosphate;
l) from about 0.005 to about 1% by weight of sucralose;
m) from about 0.005 to about 1% by weight of sodium saccharin;
n) from about 0.005 to about 0.2% by weight of calcium disodium EDTA;
o) from about 0.1 to about 2% by weight of flavoring agent; and
p) from about 0.1 to about 99% be weight of water;
said composition having a buffered pH of from about 5.5 to about 8.0.

In another embodiment, the composition disclosed is in the form of a mouthwash.

In another embodiment, the composition disclosed is substantially free of ethanol.

Further, the invention pertains to a teeth whitening composition comprising hydrogen peroxide; sodium benzoate; and trans-4-tert-butylcyclohexanol in a ratio (by weight) of any of the following:
about 25:about 2.5:about 1;
about 12.5:about 2.5:about 1;
about 6.25:about 1.25:about 1;
about 8.33:about 1.67:about 1; and
about 8.75:about 1.25:about 1;

In some embodiments, the invention pertains to a composition that comprises the ingredients of Formula 1, 2, 3, or 4, as follows:

| INCI Name | Formula 1 (% w/w) | Formula 2 (% w/w) | Formula 3 (% w/w) | Formula 4 (% w/w) |
|---|---|---|---|---|
| sodium fluoride | 0.020 | 0.050 | 0.020 | 0.020 |
| water | 79.623 | 81.295 | 75.925 | 76.875 |
| poloxamer 407 | 2.000 | 1.500 | 1.500 | 3.000 |
| propylene glycol | 2.000 | 2.500 | 2.500 | 3.000 |

-continued

| INCI Name | Formula 1 (% w/w) | Formula 2 (% w/w) | Formula 3 (% w/w) | Formula 4 (% w/w) |
|---|---|---|---|---|
| glycerin | 10.000 | 8.000 | 13.000 | 10.000 |
| hydrogen peroxide | 2.500 | 2.500 | 2.500 | 3.500 |
| sodium benzoate | 0.500 | 0.500 | 0.500 | 0.500 |
| 4-t-butylcyclohexanol | 0.006 | 0.012 | 0.009 | 0.012 |
| menthol | 0.010 | 0.050 | 0.050 | 0.050 |
| xylitol | 2.500 | 2.500 | 3.000 | 2.000 |
| sucralose | 0.200 | 0.400 | 0.400 | 0.400 |
| sodium saccharin | 0.100 | — | — | — |
| sodium phosphate | 0.100 | — | — | — |
| disodium phosphate | 0.020 | 0.100 | 0.100 | 0.050 |
| calcium disodium EDTA | 0.002 | 0.005 | 0.005 | 0.005 |

In another embodiment provided herein, there is a tooth whitening composition comprising:
a) from about 2.5% to about 5.0% by weight of hydrogen peroxide;
b) about 0.5% by weight of sodium benzoate;
c) from about 0.01% to about 0.2% by weight of 4-tert-butylcyclohexanol;
d) about 0.02% by weight of sodium fluoride;
e) about 10.0% by weight of glycerin;
f) about 2.5% by weight of xylitol;
g) about 2.0% by weight of propylene glycol;
h) about 2.0% by weight of poloxamer 407;
i) about 0.1% by weight of sodium phosphate;
j) about 0.01% by weight of menthol;
k) about 0.02% by weight of disodium phosphate;
l) about 0.2% by weight of sucralose;
m) about 0.1% by weight of sodium saccharin;
n) about 0.002% by weight of calcium disodium EDTA;
o) from about 0.1 to about 2% by weight of flavoring agent; and
p) from about 0.1 to about 99% be weight of water;
q) said composition having a buffered pH of from about 5.5 to about 8.0.

In some embodiment, the trans-4-tert-butylcyclohexanol may be present at a concentration of about 0.060% by weight of the composition or about 0.200% by weight of the composition. In some embodiments, the trans-4-tert-butylcyclohexanol is solubilized in pentylene glycol. For example, trans-4-tert-butylcyclohexanol may be solubilized in an amount of about 30% by weight of the composition trans-4-tert-butylcyclohexanol to about 70% by weight of the composition about pentylene glycol. The 30% by weight of the composition trans-4-tert-butylcyclohexanol to 70% by weight of the composition about pentylene glycol may be used in an amount of 0.200% by weight of the composition. Furthermore, trans-4-tert-butylcyclohexanol may be provided as a commercial product under the trade name SymSitive 1609® by Symrise AG. SymSitive 1609® may be used in some embodiments an amount of 0.200% by weight of the composition.

In further embodiments, hydrogen peroxide that may be present at a concentration of about 2.5% by weight of the composition or 5% by weight of the composition.

In some embodiments, the composition disclosed herein has buffered pH of from about 5.5 to about 8.0. For example the buffered pH may be about 6-7. The buffered pH of the composition may be about may be about 6.

In another embodiment, the composition disclosed herein provides a method of whitening teeth comprising contacting the tissue of oral cavity or teeth with the above-defined oral care composition for at least one minute to whiten teeth.

In some embodiments, the composition disclosed herein provides a method of whitening teeth comprising contacting the tissue of oral cavity or teeth with the above-defined oral care composition to whiten teeth.

DETAILED DESCRIPTION OF THE INVENTION

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls. Unless otherwise specified, all percentages and amounts expressed herein and elsewhere in the specification should be understood to refer to percentages by weight. The amounts given are based on the active weight of the material.

Disclosed herein are tooth whitening compositions comprising at least one whitening agent, at least one gum soother, and sodium benzoate. The tooth whitening compositions disclosed herein may further comprise other additional ingredients that include those known to one of skill in the art, including one or more of the following components: fluoride agent, oral care agent, antimicrobial agent, anti-calculus agent, surfactant, flavoring agent, sweetener, desensitizing agent, and buffering agent as will be discussed in greater detail below.

The tooth whitening composition disclosed herein can be in the form of a liquid, a semi-solid, or a solid. In some embodiments, the tooth whitening composition disclosed herein is a toothpaste, a toothpowder, a varnish, an adhesive gel, a cement, a resin, a spray, a foam, a balm, a composition carried out on a mouth strip or a buccal adhesive patch, a chewable tablet, a chewable pastille, a chewable gum, a lozenge, a beverage, a chewable gum, a lozenge, or a mouthwash, or any other form known to one of skill in the art.

Whitening Agent

In various embodiments, the tooth whitening compositions disclosed herein comprise at least one whitening agent. In certain embodiments, the at least one whitening agent is a peroxide compound. Suitable peroxide compounds include hydrogen peroxide, lithium peroxide, potassium peroxide, sodium peroxide, magnesium peroxide, calcium peroxide, barium peroxide, carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, alkyl peroxy acids, and monoperoxyphthalate and mixtures thereof. In various embodiments, the peroxide compound comprises hydrogen peroxide, urea peroxide, and sodium percarbonate and mixtures thereof.

In some embodiments disclosed herein, the at least one whitening agent may be hydrogen peroxide, and in certain exemplary embodiments, the whitening agent, for example hydrogen peroxide, may be present in the tooth whitening composition in an amount ranging from about 1 percent to about 5 percent by weight, for example about 2 percent to about 3 percent by weight, including about 2.5 percent and about 5 percent by weight, relative to the total weight of the composition.

Desensitizing Agent/Gum Soother

In various embodiments, the tooth whitening compositions disclosed herein comprise at least one desensitizing agent. Suitable desensitizing agents include cis-4-tert-butylcyclohexanol, trans-4-tert-butylcyclohexanol, potassium nitrate, gluteraldehyde, silver nitrate, zinc chloride, strontium chloride hexahydrate, sodium fluoride, stannous fluoride, strontium chloride, strontium acetate, arginine, hydroxylapatite, calcium sodium phosphosilicate, potassium oxalate, calcium phosphate, calcium carbonate, bioactive glasses, and mixtures thereof.

In some embodiments, trans-4-tert-butylcyclohexanol solubilized in pentylene glycole is used, which is available under the trade name SymSitive 1609® by Symrise AG (or equivalent thereof).

In the embodiments disclosed herein, the amount of desensitizing agent, for example trans-4-tert-butylcyclohexanol, is present in the tooth whitening composition in an amount ranging from about 0.01 percent to about 5.0 percent by weight, and in some embodiments, from about 0.1 percent to about 0.3 percent by weight, relative to the total weight of the composition. trans-4-tert-butylcyclohexanol may also be present in the tooth whitening composition in an amount about 0.01 percent by weight or about 0.20 percent by weight, about 0.06 percent by weight or about 0.20 percent by weight, including 0.06 percent relative to the total weight of the composition.

Sodium Benzoate

In various embodiments, the tooth whitening compositions disclosed herein comprises sodium benzoate. In embodiments disclosed herein, the amount of sodium benzoate is present in the tooth whitening composition in an amount ranging from about 0.1 percent to about 1.0 percent by weight, and in some embodiments, from about 0.3 percent to about 0.6 percent by weight, relative to the total weight of the composition.

Orally Acceptable/Compatible Formulation Components

The term "orally acceptable/compatible formulation components" as used herein means a suitable vehicle, which can be used to apply the present compositions to the oral cavity in a safe and effective manner. Such vehicle may include materials such as fluoride agents, antibacterial agents, anti-caries agents, buffers, other abrasive materials, peroxide sources, alkali metal bicarbonate salts, thickening materials, humectants, water, surfactants, flavoring agents, sweetening agents, cooling agents, xylitol, coloring agents, and mixtures thereof.

Fluoride Agents

In various embodiments, the tooth whitening compositions disclosed herein comprise at least one fluoride agent as the anticaries agent. Suitable free fluoride agents can be provided by sodium fluoride, stannous fluoride, indium fluoride, sodium monofluorophosphate and mixtures thereof.

In embodiments disclosed herein, the at least one fluoride agent is sodium fluoride, and in certain exemplary embodiments, the sodium fluoride is present in the tooth whitening composition in an amount ranging from about 0.01 percent to about 0.05 percent by weight, relative to the total weight of the composition.

Oral Care Agent-Xylitol

In various embodiments, the tooth whitening composition further comprises the oral care agent xylitol. In one embodiment, the tooth whitening composition comprises an amount of xylitol ranging from about 1 percent to about 5 percent by weight of the composition. In another embodiment, the amount of xylitol ranges from about 2.5 percent to about 3 percent by weight of the tooth whitening composition.

Cooling Agents

In various embodiments, the tooth whitening compositions disclosed herein comprise at least one cooling agent.

Menthol is widely used as a cooling agent. In one embodiment, the tooth whitening composition formed includes a concentration of cooling agent, for example menthol ranging from about 0.005 percent to about 0.1 percent by weight of the composition, including 0.01 percent relative to the total weight of the composition.

Surfactant

Surfactants are generally known to solubilize flavoring agents and other ingredients in a mouthwash formulation. In various embodiments, the tooth whitening compositions disclosed herein comprise at least one surfactant. Any orally acceptable surfactant, most of which are anionic, nonionic or amphoteric zwitterionic, cationic, or mixtures thereof, can be used.

Examples of anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Examples of other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed.

Another suitable surfactant is one selected from the group consisting of sarcosinate surfactants, isethionate surfactants, and taurate surfactants. In a particular embodiment, the surfactant is an alkali metal or ammonium salts of these surfactants, such as the sodium and potassium salts of the following: lauroyl sarcosinate, myristoyl sarcosinate, palmitoyl sarcosinate, stearoyl sarcosinate and oleoyl sarcosinate.

Cationic surfactants useful in the tooth whitening compositions disclosed herein include derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc.

Nonionic surfactants that can be used in the tooth whitening compositions disclosed herein include compounds produced by the condensation of alkylene oxide groups (hydrophilic in nature) with an organic hydrophobic compound which may be aliphatic or alkylaromatic in nature. Examples of suitable nonionic surfactants include the Pluronics (for example, poloxamers of the form PEO-PPO-PEO), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine Zwitterionic synthetic surfactants useful in the tooth whitening compositions disclosed herein include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

In some embodiments, the surfactants are selected from poloxamer 407, sodium hexametaphosphate, and combinations thereof.

In some embodiments, the amount of surfactant or mixtures of compatible surfactants may be present in the tooth whitening composition in an amount ranging from about 1 percent to about 3.0 percent by weight, and in another embodiment, in an amount of about 2 percent by weight of the total composition.

Humectant

A humectant can help to keep the tooth whitening composition from hardening upon exposure to air and provide a moist feel in the mouth. In some embodiments, the tooth whitening composition comprises a humectant. Suitable humectants for use in tooth whitening compositions include, but are not limited to edible polyhydric alcohols such as glycerine, sorbitol, xylitol, propylene glycol as well as other polyols and mixtures of these humectants. Mixtures of glycerine and sorbitol may be used in certain embodiments as the humectant component of the tooth whitening compositions herein.

In some embodiments, the amount of humectant or mixtures of compatible humectants may be present in the tooth whitening composition in an amount ranging from about 1 percent to about 15.0 percent by weight, in another embodiment in an amount of about 2 percent to about 10 percent, and in another embodiment in an amount of about 12 percent by weight of the total composition.

Buffering Agent

In various embodiments, the tooth whitening compositions disclosed herein comprise at least one buffering agent to adjust the pH thereof. Generally, the buffering agent should be capable of bringing the pH to a physiologically acceptable level of between about 5.5 and 8.0, and in another embodiment between about 5.5 and 6.5. A pH of 5.5 is critical for remineralization of tooth with fluoride. Anything below about pH 5.5, the rate of tooth demineralization is greater than the rate of tooth remineralization.

Exemplary buffering agents are an alkali metal or alkaline earth metal salt, and an amine (e.g., ammonium) salt of the weak carboxylic acid. In certain exemplary embodiments, the buffering agents are selected from the group consisting of sodium phosphate, phosphoric acid, disodium phosphate, citric acid, sodium citrate, calcium disodium EDTA, potassium citrate, and sodium acetate. In embodiments disclosed herein, the amount of the buffering agent may be present in the tooth whitening composition in an amount ranging from about 0.002 percent to about 1.0 percent by weight, and in some embodiments in an amount of from about 0.002 percent to about 0.2 percent by weight, relative to the total weight of the composition.

Water

In embodiments disclosed herein, water is present in the tooth whitening compositions disclosed herein. Water commonly makes up the balance of the compositions and includes 0.1 to 99%, and in some embodiments from 10% to 90%, and in some embodiments from 70% to 80% by weight of the tooth whitening compositions. This amount of water includes free water which is added plus that amount which is introduced with other materials such as with hydrogen peroxide or any components of the composition.

Ethyl Alcohol

In some embodiments, the tooth whitening composition is substantially free of ethyl alcohol. "Substantially free" means having less than 0.5 percent to the total weight of the composition. In other embodiments, the tooth whitening composition is free of ethyl alcohol.

Flavoring Agents

In various embodiments, the tooth whitening compositions disclosed herein comprise at least one flavoring agent.

Illustrative examples of the flavoring agent suited for inclusion into the composition include, but are not limited to menthol, wintergreen, methyl salicylate, cassia, 1-menthyl acetate, sage, parsley oil, oxanone, marjoram, lemon, orange, propenyl guaethol, vanillin, thymol, linalool, mint flavor (eg. fresh mint, peppermint, spearmint, fresh mint AC114897 (ArylEssence (G.A., USA), N&A Cool Mint (646556) (Symrise, N.J.), and flavoring agents that provide a tingling sensation, such as spilanthol, and mixtures thereof (for example, Sensingle branded mixture TAK112683 (Takasago (Tokyo, Japan)). Flavoring agents are generally used in the compositions at levels of from about 0.1 percent to about 0.3 percent, and in another embodiment about 0.2 percent to 0.3 percent by weight of the total composition.

Sweeteners

In various embodiments, the tooth whitening composition further comprises at least one sweetener. These sweeteners are, for example, sorbitol, xylitol, asparatame, sucrose, glucose, saccharin, dextrose, levulose, lactose, mannitol, sorbitol, fructose, maltose, saccharin salts, thaumatin, D-tryptophan, dihydrochalcones, acesulfame or cyclamate salts and mixtures thereof. Additionally, any mixture of sweetening agents having an equivalent sweetening effect and compatible to the tooth whitening composition is contemplated within the term of sweetening agents. In one embodiment, sweeteners such as glycerin, xylitol, sodium saccharin, and sucralose are added to soothe any remaining slight irritation caused by hydrogen peroxide and its decomposition products.

In one embodiment, the sweetener is present in the composition at a concentration of from 0 percent to about 0.5 percent by weight of the total, and in another embodiment in an amount about 0.1 percent to about 0.2 percent by weight of the total composition.

As used herein, the term "about" refers to a ±10% variation from the nominal value. It is to be understood that such a variation is always included in any given value provided herein, whether or not it is specifically referred to.

EXAMPLES

The following examples will further illustrate the embodiments disclosed herein, without, however, limiting it thereto.

Formula 1-5 are prepared with the following ingredients:

| INCI Name | Formula 1 (% w/w) | Formula 2 (% w/w) | Formula 3 (% w/w) | Formula 4 (% w/w) | Formula 5 (% w/w) |
| --- | --- | --- | --- | --- | --- |
| sodium fluoride | 0.020 | 0.050 | 0.020 | 0.020 | 0.020 |
| water | 79.623 | 81.295 | 75.925 | 76.875 | 77.123 |
| poloxamer 407 | 2.000 | 1.500 | 1.500 | 3.000 | 2.000 |
| propylene glycol | 2.000 | 2.500 | 2.500 | 3.000 | 2.000 |
| glycerin | 10.000 | 8.000 | 13.000 | 10.000 | 10.000 |
| hydrogen peroxide | 2.500 | 2.500 | 2.500 | 3.500 | 2.500 |
| sodium benzoate | 0.500 | 0.500 | 0.500 | 0.500 | 0.500 |
| 4-t-butylcyclo-hexanol | 0.006 | 0.012 | 0.009 | 0.012 | 0.006 |
| menthol | 0.010 | 0.050 | 0.050 | 0.050 | 0.010 |
| xylitol | 2.500 | 2.500 | 3.000 | 2.000 | 2.500 |
| Sensingle (TAK112683) | 0.005 | — | — | — | 0.005 |
| Fresh Mint (AC114897) | 0.220 | — | — | — | 0.220 |
| N&A Cool Mint (646556) | — | 0.200 | 0.200 | 0.200 | — |
| sucralose | 0.200 | 0.400 | 0.400 | 0.400 | 0.200 |
| sodium saccharin | 0.100 | — | — | — | 0.100 |
| sodium phosphate | 0.100 | — | — | — | 0.100 |
| disodium phosphate | 0.020 | 0.100 | 0.100 | 0.050 | 0.020 |
| calcium disodium EDTA | 0.002 | 0.005 | 0.005 | 0.005 | 0.002 |

Simple Optimal Manufacturing Process

The following ingredients were pre-blended in a separate mixing vessel: propylene glycol, menthol, Symsitive, Sensingle, and Fresh Mint materials. In a separate main mixing tank, the following ingredients were added sequentially: water, sodium fluoride, sodium benzoate, monosodium phosphate, disodium phosphate, calclium disodium EDTA, sodium saccharin, and sucralose. Poloxamer 407 was sprinkled slowly onto the main tank. Glycerin, xylitol, and hydrogen peroxide were added prior to the addition of pre-blended propylene glycol solution above. The above mixture was mixed for at least 60 minutes to ensure a homogeneous clear emulsion was obtained.

Treatment of Subjects Using Tooth Whitening Composition In Vivo Whitening of the Stained Teeth-Clinical Study The tooth whitening composition of Formula 1 above was used in the Whitening clinical study as Treatment A. Three commercial products are used for comparison: treatment B is Competitor B; treatment C is Competitor C and treatment D is Control D. Users were instructed to rinse with the mouthwash according to the respective mouthwash's label usage and directions. Examinations were performed before treatment on the first day (baseline), and after treatment on Days 4, 5, 6 and 7 and at 2 weeks. Additionally, there was a second phase where subjects were followed for 4 weeks of additional treatment to see if the test products help keep stains from re-forming. Baseline for this second phase analysis is the stain score at two week intervals with additional evaluations at Weeks 4 and 6. The data used in the statistical analysis are the changes from baseline at each post-treatment time point for each tooth, averaged for each subject. At each time of examination, each user's teeth were photographed and the staining was scored.

| INCI Name | Treatment A (ACT whitening mouthwash) | Treatment B (Listerine) | Treatment C (CREST 3D) | Treatment D (ACT CONTROL PRODUCT) |
| --- | --- | --- | --- | --- |
| Sodium fluoride | 0.02 | 0.02 | — | 0.05 |
| Hydrogen peroxide | 2.5 | 2.67 | 1.5 | absent |
| Ethyl Alcohol | absent | 0.08 | — | absent |
| Sodium benzoate | 0.5 | absent | absent | 0.5 |
| 4-t-butylcyclohexanol | 0.06 | absent | absent | absent |

Vita Shade Study

The level of stain on the subjects' teeth was evaluated using the Vita Shade Guide Method of Tooth Color Assessment. This standardized shade guide which is used by the dental profession includes sixteen different shades. Additionally, there was a second phase where subjects were followed for 4 weeks of additional treatment to see if the test products help keep stains from re-forming. Baseline for this second phase analysis is the stain score at two week intervals with additional evaluations at Weeks 4 and 6. The data used in the statistical analysis are the changes from baseline at each post-treatment time point for each tooth, averaged for each subject.

The data used in the statistical analysis are the changes from baseline at each post-treatment time point.

Statistical Analysis

In order to evaluate the clinical results, analysis was conducted using paired t-test. Additionally, the number/percentage of subjects indicating a reduction was summarized.

Results

The results in Table I demonstrate that Treatment A provides faster whitening effect compared to commercial products. After 4 days, Treatment A provides 6.8% reduction from baseline, compared to 0.7% for Competitor Treatment B and 3.5% for Treatment C.

Furthermore, the results in Table I demonstrate that Treatment A provides more efficient whitening effect compared to commercial products. After 6 weeks, Treatment A provides 41.6% reduction from baseline, compared to 20% for Competitor Treatment B and 23.2% for Competitor Treatment C.

TABLE 1

Vita Shade - Changes from Baseline

|  | Treatment A | | Treatment B | | Treatment C | | Treatment D | |
| --- | --- | --- | --- | --- | --- | --- | --- | --- |
|  | Treatment Mean | Percent Reduction | Treatment Mean | Percent Reduction | Treatment Mean | Percent Reduction | Treatment Mean | Percent Reduction |
| Baseline | 8.54 |  | 8.44 |  | 8.55 |  | 8.75 |  |
| Day 4 | 7.96 | −6.8% | 8.43 | −0.7% | 8.33 | −3.5% | 9.00 | 3.8% |
| Day 5 | 7.25 | −14.6% | 7.87 | −6.1% | 7.80 | −9.2% | 8.86 | 2.2% |
| Day 6 | 6.99 | −19.1% | 7.72 | −8.5% | 7.50 | −12.4% | 8.89 | 0.7% |
| Day 7 | 6.24 | −26.7% | 7.18 | −13.3% | 7.35 | −14.0% | 8.61 | −1.6% |
| 2 Weeks | 5.83 | −32.1% | 7.34 | −12.8% | 7.17 | −15.3% | 8.78 | 1.5% |
| 4 Weeks | 5.68 | −33.4% | 6.89 | −16.9% | 7.00 | −18.0% | 8.60 | −0.9% |
| 6 Weeks | 5.04 | −41.6% | 6.67 | −20.0% | 6.49 | −23.2% | 8.35 | −5.3% |

Safety

Safety evaluations consisted of erythema and edema scores of the buccal and sublingual mucosa, attached gingiva and the tongue. Evaluations were conducted at Baseline and at each post-treatment evaluation. A frequency table of responses summarizes the erythema and edema scores at each time point.

TABLE 2

Safety assessment - Changes from Baseline*

|  |  | Right Buccal | | Left Buccal | | Sublingual | | Gingiva | | Tongue | |
| --- | --- | --- | --- | --- | --- | --- | --- | --- | --- | --- | --- |
|  |  | Erythema | Edema | Erythema | Edema | Erythema | Edema | Erythema | Edema | Erythema | Edema |
| Treatment A | Baseline |  |  |  |  |  |  |  |  |  |  |
|  | Day 7 | −0.01 | 0.00 | −0.01 | 0.00 | −0.01 | 0.00 | −0.07 | −0.01 | −0.01 | 0.00 |
|  | 2 Weeks | −0.01 | 0.00 | −0.01 | 0.00 | −0.01 | 0.00 | −0.06 | −0.01 | −0.01 | 0.00 |
|  | 4 Weeks | −0.01 | 0.00 | −0.01 | 0.00 | −0.01 | 0.00 | −0.06 | −0.01 | −0.01 | 0.00 |
|  | 6 Weeks | −0.01 | 0.00 | −0.01 | 0.00 | −0.01 | 0.00 | −0.07 | −0.01 | −0.01 | 0.00 |
| Treatment B | Baseline |  |  |  |  |  |  |  |  |  |  |
|  | Day 7 | −0.01 | 0.00 | −0.01 | 0.00 | −0.01 | 0.00 | −0.09 | −0.04 | −0.01 | 0.00 |
|  | 2 Weeks | −0.01 | 0.00 | −0.01 | 0.00 | −0.01 | 0.00 | −0.09 | −0.05 | −0.01 | 0.00 |
|  | 4 Weeks | −0.01 | 0.00 | −0.01 | 0.00 | −0.01 | 0.00 | −0.10 | −0.05 | −0.01 | 0.00 |
|  | 6 Weeks | −0.01 | 0.00 | −0.01 | 0.00 | −0.01 | 0.00 | −0.10 | −0.05 | −0.01 | 0.00 |
| Treatment C | Baseline |  |  |  |  |  |  |  |  |  |  |
|  | Day 7 | 0.00 | 0.00 | 0.00 | 0.00 | 0.00 | 0.00 | −0.07 | 0.00 | 0.00 | 0.00 |
|  | 2 Weeks | 0.00 | 0.00 | 0.00 | 0.00 | 0.00 | 0.00 | −0.08 | 0.00 | 0.00 | 0.00 |
|  | 4 Weeks | 0.00 | 0.00 | 0.00 | 0.00 | 0.00 | 0.00 | −0.08 | 0.00 | 0.00 | 0.00 |
|  | 6 Weeks | 0.00 | 0.00 | 0.00 | 0.00 | 0.00 | 0.00 | −0.08 | 0.00 | 0.00 | 0.00 |

TABLE 2-continued

| | | Right Buccal | | Left Buccal | | Sublingual | | Gingiva | | Tongue | |
|---|---|---|---|---|---|---|---|---|---|---|---|
| | | Erythema | Edema | Erythema | Edema | Erythema | Edema | Erythema | Edema | Erythema | Edema |
| Treatment D | Baseline | | | | | | | | | | |
| | Day 7 | 0.00 | 0.00 | 0.00 | 0.00 | 0.00 | 0.00 | −0.13 | −0.03 | 0.00 | 0.00 |
| | 2 Weeks | 0.00 | 0.00 | 0.00 | 0.00 | 0.00 | 0.00 | −0.10 | −0.03 | 0.00 | 0.00 |
| | 4 Weeks | 0.00 | 0.00 | 0.00 | 0.00 | 0.00 | 0.00 | −0.10 | −0.03 | 0.00 | 0.00 |
| | 6 Weeks | 0.00 | 0.00 | 0.00 | 0.00 | 0.00 | 0.00 | −0.10 | −0.03 | 0.00 | 0.00 |

*the data for Day 7, 2 weeks, 4 weeks, and 6 weeks, listed in the foregoing table represent the "mean difference from the baseline"

The results in Table 2 demonstrate that Treatment A provides reduction in the gingival erythema from baseline.

What is claimed is:

1. A tooth whitening composition comprising:
   a) from about 1.0% to about 5.0% by weight of hydrogen peroxide;
   b) from about 0.1% to about 1.0% by weight of sodium benzoate;
   c) from about 0.01% to about 0.5% by weight of 4-tert-butylcyclohexanol; and
   an orally acceptable formulation component.

2. The tooth whitening composition according to claim 1, wherein the composition is in a form selected from the group consisting of a toothpaste, dentifrice, rinse, gel, edible film, lozenge, spray, tooth powder, subgingival gel, mouthwash and denture product.

3. The tooth whitening composition according to claim 1, further comprising one or more components selected from the group consisting of:
   a) a fluoride agent;
   b) an oral care agent;
   c) a cooling agent;
   d) a surfactant;
   e) a humectant; and
   f) a buffering agent.

4. The tooth whitening composition according to claim 3, wherein said composition further comprises a flavoring agent and a sweetener.

5. The tooth whitening composition according to claim 4, wherein the fluoride agent is sodium fluoride; the oral care agent is xylitol; the cooling agent is menthol; the surfactant is selected from poloxamer 407, sodium hexametaphosphate and combinations thereof; the humectant is selected from propylene glycol and glycerin; and the buffering agent is selected from sodium phosphate, disodium phosphate and calcium disodium EDTA.

6. The tooth whitening composition according to claim 4, wherein the composition comprises:
   a) from about 1.0% to about 5.0% by weight of hydrogen peroxide;
   b) from about 0.1% to about 1.0% by weight of sodium benzoate;
   c) from about 0.01% to about 0.5% by weight of 4-tert-butylcyclohexanol; and
   d) from about 0.01% to about 0.05% by weight of sodium fluoride.

7. The tooth whitening composition according to claim 4, wherein the composition comprises:
   a) from about 1.0% to about 5.0% by weight of hydrogen peroxide;
   b) from about 0.1% to about 1.0% by weight of sodium benzoate;
   c) from about 0.01% to about 0.5% by weight of 4-tert-butylcyclohexanol;
   d) from about 0.01% to about 0.05% by weight of sodium fluoride;
   e) from about 5.0 to about 15.0% by weight of glycerin;
   f) from about 1.0 to about 5.0% by weight of xylitol;
   g) from about 1.0 to about 3.0% by weight of propylene glycol; and
   h) from about 1.0 to about 3.0% by weight of poloxamer 407.

8. The tooth whitening composition according to claim 4, wherein the composition comprises:
   a) from about 1.0% to about 5.0% by weight of hydrogen peroxide;
   b) from about 0.1% to about 1.0% by weight of sodium benzoate;
   c) from about 0.01% to about 0.5% by weight of 4-tert-butylcyclohexanol;
   d) from about 0.01% to about 0.05% by weight of sodium fluoride;
   e) from about 5.0 to about 15.0% by weight of glycerin;
   f) from about 1.0 to about 5.0% by weight of xylitol;
   g) from about 1.0 to about 3.0% by weight of propylene glycol;
   h) from about 1.0 to about 3.0% by weight of poloxamer 407;
   i) from about 0.01 to about 0.3% by weight of monosodium phosphate; and
   j) from about 0.005 to about 0.2% by weight of disodium phosphate.

9. The tooth whitening composition according to claim 4, wherein the composition comprises:
   a) from about 1.0% to about 5.0% by weight of hydrogen peroxide;
   b) from about 0.1% to about 1.0% by weight of sodium benzoate;
   c) from about 0.01% to about 0.5% by weight of 4-tert-butylcyclohexanol;
   d) from about 0.01% to about 0.05% by weight of sodium fluoride;
   e) from about 5.0 to about 15.0% by weight of glycerin;
   f) from about 1.0 to about 5.0% by weight of xylitol;
   g) from about 1.0 to about 3.0% by weight of propylene glycol;
   h) from about 1.0 to about 3.0% by weight of poloxamer 407;
   i) from about 0.01 to about 0.3% by weight of monosodium phosphate;
   j) from about 0.005 to about 0.1% by weight of menthol;
   k) from about 0.005 to about 0.2% by weight of disodium phosphate;
   l) from about 0.005 to about 1% by weight of sucralose;

m) from about 0.005 to about 1% by weight of sodium saccharin;
n) from about 0.005 to about 0.2% by weight of calcium disodium EDTA;
o) from about 0.1 to about 2% by weight of flavoring agent; and
p) from about 0.1 to about 99% be weight of water;
said composition having a buffered pH of from about 5.5 to about 8.0.

10. The composition of claim 1, wherein the composition is in the form of a mouthwash.

11. The composition of claim 1, wherein the composition is substantially free of ethanol.

12. A method of whitening teeth comprising contacting the tissue of oral cavity or teeth with a tooth whitening composition according to claim 1 to whiten teeth.

13. A tooth whitening composition comprising:
a) from about 2.5% to about 5.0% by weight of hydrogen peroxide;
b) about 0.5% by weight of sodium benzoate;
c) from about 0.01% to about 0.2% by weight of 4-tert-butylcyclohexanol;
d) about 0.02% by weight of sodium fluoride;
e) about 10.0% by weight of glycerin;
f) about 2.5% by weight of xylitol;
g) about 2.0% by weight of propylene glycol;
h) about 2.0% by weight of poloxamer 407;
i) about 0.1% by weight of sodium phosphate;
j) about 0.01% by weight of menthol;
k) about 0.02% by weight of disodium phosphate;
l) about 0.2% by weight of sucralose;
m) about 0.1% by weight of sodium saccharin;
n) about 0.002% by weight of calcium disodium EDTA;
o) from about 0.1 to about 2% by weight of flavoring agent; and
p) from about 0.1 to about 99% be weight of water;
q) said composition having a buffered pH of from about 5.5 to about 8.0.

14. The composition of claim 13, wherein the hydrogen peroxide is present in a concentration of 5% by weight of the composition.

15. The composition of claim 13, wherein the hydrogen peroxide is present in a concentration of 2.5% by weight of the composition.

16. The composition of claim 13, wherein the 4-t-butyl-cyclohexanol is present in a concentration of 0.06% by weight of the composition.

17. The composition of claim 13, wherein the 4-t-butyl-cyclohexanol is present in a concentration of 0.20% w/w by weight of the composition, and wherein the 4-t-butylcyclohexanol is solubilized in an amount of about 30% trans-4-tert-butylcyclohexanol to about 70% w about pentylene glycol by weight of the composition.

* * * * *